United States Patent [19]

Post

[11] 4,187,299
[45] Feb. 5, 1980

[54] FORTIMICIN E

[75] Inventor: Gerald G. Post, Kenosha, Wis.

[73] Assignee: Abbott Laboratories, Chicago, Ill.

[21] Appl. No.: 863,016

[22] Filed: Dec. 21, 1977

[51] Int. Cl.$^2$ ................. A61K 31/71; C07H 15/22
[52] U.S. Cl. ............................ 424/181; 536/4; 536/17 R; 435/80; 435/867
[58] Field of Search ............... 536/17, 13, 4; 424/181

[56] References Cited

U.S. PATENT DOCUMENTS

| | | | |
|---|---|---|---|
| 3,931,400 | 1/1976 | Nara et al. | 536/17 |
| 3,976,768 | 8/1976 | Nara et al. | 424/118 |
| 3,985,727 | 10/1976 | Daniels | 536/17 |

*Primary Examiner*—Johnnie R. Brown
*Attorney, Agent, or Firm*—Robert L. Niblack; Gildo E. Fato; Joyce R. Niblack

[57] ABSTRACT

A new aminoglycoside antibiotic, Fortimicin E, is produced by fermentation of *Micromonospora olivoasterospora* ATCC 21819, 31009 and 31010 and isolated from the fermentation broth.

3 Claims, No Drawings

FORTIMICIN E

BACKGROUND OF THE INVENTION

Despite the availability of a variety of highly effective antibiotics, the search for new antibiotics is a continuing one. The primary reason for the continuing search is the reoccurring development of microorganisms which are resistant to existing antibiotic therapy. Thus there is a continuing need for new antibiotics which are either intrinsically more active than existing drug entities and thus can be administered in lower dosages to minimize the side effects of these powerful drugs, or are effective against resistant strains.

A number of aminoglycoside antibiotics are known, such as the gentamicin and kanamycin family of antibiotics. More recently, a new family of aminoglycosides, the fortimicins have been indentified. See, for example, U.S. Pat. Nos. 3,976,768 and 3,931,400.

Although the fortimicin family is a relatively new group of antibiotics, clinical experience has shown that amino-glycoside antibiotics are susceptible to the resistant strain problem. In many cases, the resistance is R-factor mediated and is attributed to the ability of the bacteria to enzymatically modify the amino or hydroxy groups of the aminoglycoside antibiotics.

The compound of this invention, fortimicin E, is a 3,4-di-epi isomer of fortimicin B. Fortimicin E is more selective in its antibacterial spectrum, and is useful as an intermediate for preparing new fortimicin derivatives.

Thus there is a continuing need for new antibiotic entities in this valuable antibiotic family. The present invention provides an intermediate for preparing such entities, i.e. 4-N-acyl fortimicin E derivatives.

SUMMARY OF THE INVENTION

The present invention provides a new antibiotic, fortimicin E, which is provided by the fermentation of *Micromonospora olivoasterospora* ATCC No. 21819, 31009 or 31010. The antibiotic is isolated from the fermentation broth by ion exchange and silica gel chromatographic techniques.

DETAILED DESCRIPTION OF THE INVENTION

Fortimicin E represented by the formula

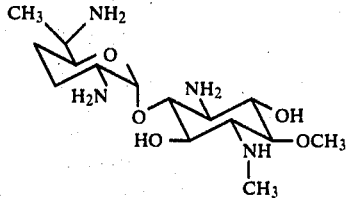

Fortimicin E is co-produced along with Fortimicin A and B by the fermentation of *Micromonospora olivoasterospora* ATCC 21819, 31009 or 31010 in a suitable nutrient medium as taught in U.S. Pat. No. 3,931,400. Isolation and purification of fortimicin E from the fermentation broth is accomplished by adsorption and desorption from suitable cation exchange resins, carbon and chromatography on silica gel as discussed in detail hereinbelow.

Fortimicin E exhibits anti-bacterial activity against various Gram-positive and Gram-negative bacteria. The antibiotic can be employed in daily dosages of from 10 to 100 mg/kg, by injectable routes of administration and can further be used as a surface disinfectant for controlling the population of various bacteria.

The pharmaceutically acceptable salts of fortimicin E are also included within the scope of this invention. The term "pharmaceutically acceptable salts" refers to non-toxic acid addition salts of fortimicin E which are generally prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

In addition to its antibiotic activity, fortimicin E is useful as an intermediate in preparing fortimicin E derivatives, which are useful as antibiotics, such as 4-N-aminoacyl fortimicin E derivatives disclosed in a co-pending, concurrently filed and co-assigned U.S. Patent Application, Ser. No. 863,010.

Generally speaking, conventional methods for culturing microorganisms of the Actinomycetes may be employed in the process of the present invention. Thus, various nutrient sources may be employed for the culture medium. Appropriate carbon sources include glucose, starch, mannose, fructose, sucrose, molasses, etc. either alone or in combination. Additionally, hydrocarbons, alcohols, organic acids, etc., may be used depending upon the ability of utilization possessed by the particular strain of microorganism. Inorganic and organic nitrogen sources such as ammonium chloride, ammonium sulfate, urea, ammonium nitrate, sodium nitrate, etc., and natural nitrogen sources such as peptone, meat extract, yeast extract, dry yeast, corn steep liquor, soybean meal, casamino acid, soluble vegetable protein, etc., may be used alone or in combination. In addition, such inorganic salts as sodium chloride, potassium chloride, calcium carbonate, phosphates, etc. may be added to the medium, if necessary. Furthermore, organic or inorganic materials capable of promoting growth of the microorganism and the production of fortimicin E may be properly added to the medium.

A liquid culturing method, especially a submerged stirring culture method, is most suitable for the present process. It is desirable to carry out culturing at a temperature of 25° to 40° C. and at an approximately neutral pH. The antibiotic of the present invention is formed and accumulated in the culture liquor usually 4 to 15 days of culturing. When the yield of fortimicin E in the culture liquor reaches a maximum, culturing is discontinued and the antibiotic is isolated and purified from the culture liquor obtained after the microbial cells have been removed such as by filtration.

Isolation and purification of fortimicin E from the filtrate is carried out according to the methods usually used in the isolation and purification of microbial metabolic products from culture liquor.

Since fortimicin E is basic and is soluble in water, but poorly soluble in the ordinary organic solvents, the antibiotic can be purified by the methods usually used for the purification of so-called water-soluble basic antibiotics. More specifically, fortimicin E may be purified by a proper combination of adsorption and desorption from cation exchange resins, column chromatography using silica gel chromatography and the like methods.

The following examples illustrate the preferred method of producing and isolating fortimicin E from the fermentation broth.

EXAMPLE I

Preparation of Fermentation Broth

6000 Liters of a fermentation broth having the following composition and pH 7 before sterilization is prepared:

| Ingredient | Weight Percent |
|---|---|
| Starch | 4.00 |
| Soybean meal | 2.00 |
| Cornsteep liquor | 0.05 |
| $K_2HPO_4$ | 0.05 |
| $MgSO_4-7H_2O$ | 0.05 |
| KCl | 0.03 |
| $CaCO_3$ | 0.1 |
| Water | to 100.00 |

EXAMPLE II

Preparation of Inoculum

*Micromonospora olivoasterospora* ATCC 21819 is used as a seed strain and is initially cultured in a first seed medium containing 2% glucose, 0.5% peptone, 0.5% yeast extract and 0.1% calcium carbonate (ph 7.2 before sterilization) by inoculating one loopful of the seed strain into 10 ml of the seed medium in a 50 ml large test tube. Culturing is carried out at 30° C. for 5 days with shaking. Ten ml of the seed culture broth is then incoluated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a 2 l Erlenmeyer flask provided with baffles. The composition of the third seed medium is the same as that of the second seed medium and the third seed culturing is carried out at 30° C. for 2 days with shaking. Thereafter 1.5 l of the third seed culture broth (corresponding to the content of five flasks) is inoculated into 15 l of a fourth seed medium in a 30 l glass jar fermenter. The composition of the fourth seed medium is the same as that of the first seed medium. Culturing in the jar fermenter is carried out at 30° C. for two days with aeration and stirring (revolution: 350 r.p.m., aeration: 15 l/min).

EXAMPLE III

Production of Fortimicin E 15 l of the fourth seed culture broth of Example II is inoculated into 150 l of a main fermentation medium in a 300 l stainless steel fermenter. The main fermentation medium comprises: 4% starch, 2% soybean meal, 1% corn steep liquor, 0.5% $K_2HPO_4$, 0.05% $MgSO_4.7H_2O$, 0.03% KCl and 0.1% $CaCO_3$ and water (pH 7.0 before sterilization). Culturing in the fermenter is carried out at 30° C. for 4 days with aeration and stirring (revolution: 150 r.p.m.; aeration: 80 l/min).

EXAMPLE IV

Isolation of Fortimicin E

To 5000 liters of the fermentation broth prepared as above described is added 102 liters of a weakly acidic carboxylic (polymethacrylate) type cation exchange resin in the ammonia form, e.g. Amberlite IRC-50 sold by Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The column is washed with water, then eluted downflow with 1 N ammonium hydroxide. Elutes of pH 9.6 to about 11.3 are collected and concentrated under reduced pressure until excess ammonia is removed. The solution is adjusted to pH 2.0 with hydrochloric acid and treated with 5% (w/v) activated carbon such as Pittsburgh RB carbon sold by Calgon Corporation. The solution is then is filtered through a diatomaceous earth mat and the filtrate concentrated under reduced pressure to give a mixture of crude fortimicins and metabolites.

A portion of the crude fortimicins (265 grams), prepared as described above, is dissolved in 8 liters of water and the solution adjusted to pH 9.0 with ammonium hydroxide. To facilitate isolation of fortimicin E, fortimicin A is hydrolyzed to fortimicin B by heating the solution to 70% for 20 hours, maintaining pH 9.0 by the controlled addition of ammonium hydroxide. After filtration through a mat of diatomaceous earth, the reaction mixture is concentrated under reduced pressure to approximately 3.6 liters. A portion of this material (1.8 liters) is diluted to 15 liters with water and adjusted to pH 6.8 with hydrochloric acid. The solution is charged on a column containing 7 liters of a weakly acidic, carboxylic (polymethacrylic) type, cation exchange resin in the ammonia form, e.g. Amberlite IRC-50. After washing with water, the column is eluted with 20 liters of 0.1 N ammonium hydroxide. One liter fractions are collected and examined by thin layer chromatography. Development is carried out at room temperature using a solvent system consisting of the lower phase of a mixture of methanol-chlorform-concentrated ammonium hydroxide (1:1:1 v/v).

Fractions 1–2: Unidentified minor components
Fraction 3–4: Isofortimicin
Fraction 5: Isofortimicin and fortimicin B
Fraction 6–10: Fortimicin B
Fractions 11–20: Unidentified minor components Continued elution of the column with 1 N ammonium hydroxide gives fractions containing fortimicin E as the major component. Lyphilization of the latter fractions yields 22 g. of fortimicin E.

An analytical sample of fortimicin E is prepared by further chromatography on a column of silic gel, prepared and eluted with a solvent system consisting of the lower phase of a mixture of methanol-chloroform-concentrated ammonium hydroxide (1:1:1: v/v/v). Chromatography of 1 g. of crude fortimicin E, prepared as described above, yields 0.632 g. of pure antibiotic as the free base.

EXAMPLE V

Preparation of Fortimicin E Tetrahydrochloride

The tetrahydrochloride salt of fortimicin E is prepared by dissolving 3.48 g. of fortimicin E in a solution of 0.2 N hydrochloric acid in methanol. The solution is taken to dryness under reduced pressure and the excess hydrochloric acid is removed by repeated coevaporation with methanol, yielding 4.95 g. of fortimicin E tetrahydrochloride as a white powder; $[\alpha]_D^{24} + 56.5°$ (c 1.0, CH$_3$OH); IR (KBr) 3420, 2930, 1585 and 1482 cm$^{-1}$; NMR (D$_2$O) δ 1.8 (C$_{6'}$—CH$_3$, J$_{6',7'}$=7.0 Hz), 4.14 (C$_3$—OCH$_3$), 6.34 (H$_{1'}$, J$_{1'2'}$=3.2 Hz).

The in vitro antibiotic activity is determined by a 2-fold agar delution method using 10 ml. per petri plate of Mueller-Hinton agar. The agar is innoculated with one loopful (0.001 ml. loop) of a 1:10 dilution of a 24 hour broth culture of the indicated test organism and incubated at 37° C. for 24 hours.

The invention includes within its scope pharmaceutical compositions comprising, as an active ingredient, fortimicin E or a pharmaceutically acceptable salt thereof in association with a pharmaceutical carrier or diluent. The compounds of this invention can be administered by parenteral (intramuscular, intraperitoneal, intravenous, subcutaneous injection routes) or rectal routes of administration and can be formulated in dosage forms appropriate for each route of administration.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are preferably suppositories which may contain, in addition to the active substane, excipients such as cocoa butter or a suppository wax.

The dosage of active ingredient in the compositions of this invention may be varied; however, it is necessary that the amount of active ingredient shall be such that a suitable dosage form is obtained. The selected dosage depends upon the desired therapeutic effect, on the route of administration, and on the duration of the treatment. Generally, dosage levels of between 10 to 100 mg/kg. of body weight daily are administered to mammalian patients to achieve an antibiotic effect.

I claim:

1. Fortimicin E, represented by the formula

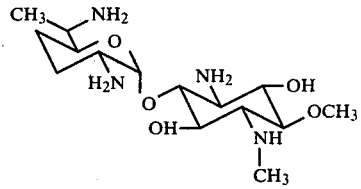

or a pharmaceutically acceptable salt thereof.

2. Fortimicin E tetrahydrochloride.

3. A pharmaceutical composition comprising a therapeutically effective amount of fortimicin E or a pharmaceutically acceptable salt thereof and a pharmaceutically acceptable carrier or diluent.

* * * * *